United States Patent
Bral

(10) Patent No.: US 7,726,821 B2
(45) Date of Patent: Jun. 1, 2010

(54) MEANS AND METHOD TO PREVENT LIQUIDS AND FLYING DEBRIS FROM BLOCKING THE VIEWING PATHWAY OF AN OPTICAL ELEMENT

(76) Inventor: Pourang Bral, 155 Albion St., Passaic, NJ (US) 07055

( * ) Notice: Subject to any disclaimer, the term of this patent is extended or adjusted under 35 U.S.C. 154(b) by 666 days.

(21) Appl. No.: 11/396,779

(22) Filed: Apr. 3, 2006

(65) Prior Publication Data

US 2007/0229954 A1    Oct. 4, 2007

(51) Int. Cl.
*G02B 23/16* (2006.01)
*G03B 11/04* (2006.01)

(52) U.S. Cl. .................... 359/511; 359/507

(58) Field of Classification Search ............. 359/507, 359/509, 511, 513; 433/31, 116; 600/133, 600/138, 139, 155, 156, 157, 158
See application file for complete search history.

(56) References Cited

U.S. PATENT DOCUMENTS

| | | | | |
|---|---|---|---|---|
| 759,622 A * | 5/1904 | Lake | .................... | 359/509 |
| 897,290 A * | 9/1908 | Jacobs | .................... | 2/433 |
| 1,222,156 A * | 4/1917 | Steinmetz | .................... | 359/509 |
| 1,357,887 A * | 11/1920 | Mickelson | .................... | 359/894 |
| 2,862,299 A * | 12/1958 | Reiter | .................... | 433/31 |
| 4,279,594 A * | 7/1981 | Rigutto | .................... | 433/31 |
| 4,497,550 A * | 2/1985 | Ouchi et al. | .................... | 359/509 |
| 4,646,722 A * | 3/1987 | Silverstein et al. | .................... | 600/104 |
| 4,991,564 A * | 2/1991 | Takahashi et al. | .................... | 600/124 |
| 5,386,817 A * | 2/1995 | Jones | .................... | 600/104 |
| 5,460,168 A * | 10/1995 | Masubuchi et al. | .................... | 600/123 |
| 5,643,175 A * | 7/1997 | Adair | .................... | 600/133 |
| 5,733,244 A * | 3/1998 | Yasui et al. | .................... | 600/127 |
| 2008/0045791 A1 * | 2/2008 | Gal et al. | .................... | 600/116 |

* cited by examiner

*Primary Examiner*—Ricky D Shafer

(57) ABSTRACT

The invention comprises of a means and a method to keep clean a plurality of transparent surfaces, through which a plurality of images are captured by an optical element, which may be an optical sensor or a camera, where there is flying debris or liquids or liquids that can potentially stick to a plurality of said transparent surfaces and clog the view of said optical element. A plurality of channels transfer and direct fluid such as compressed air from an outside source to blow over and keep a plurality of said transparent surfaces free of debris or liquids.

11 Claims, 6 Drawing Sheets

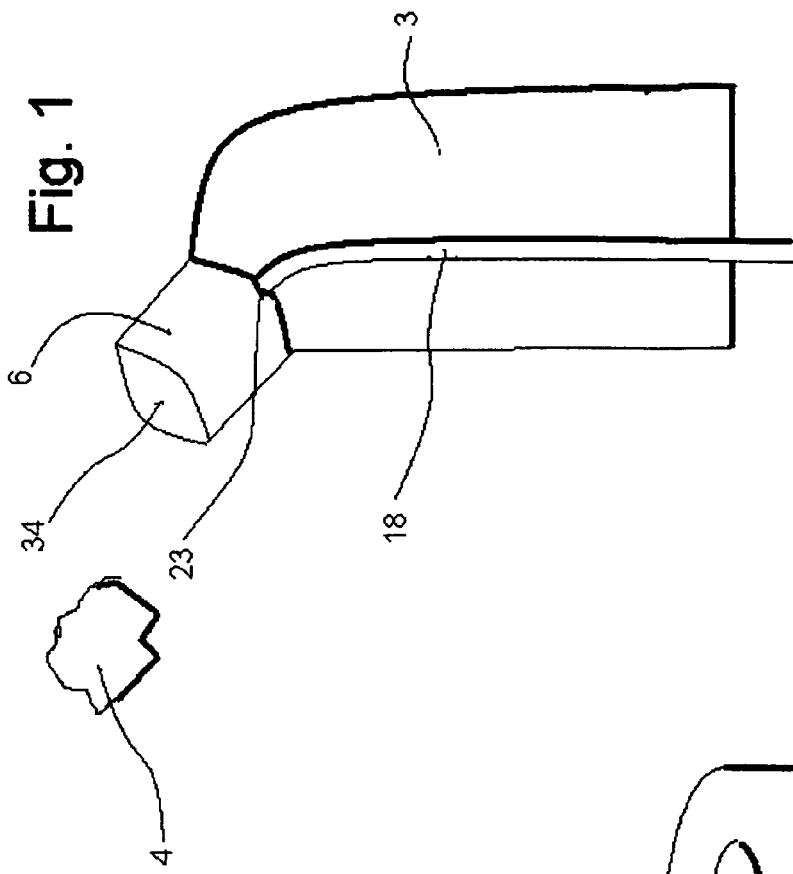
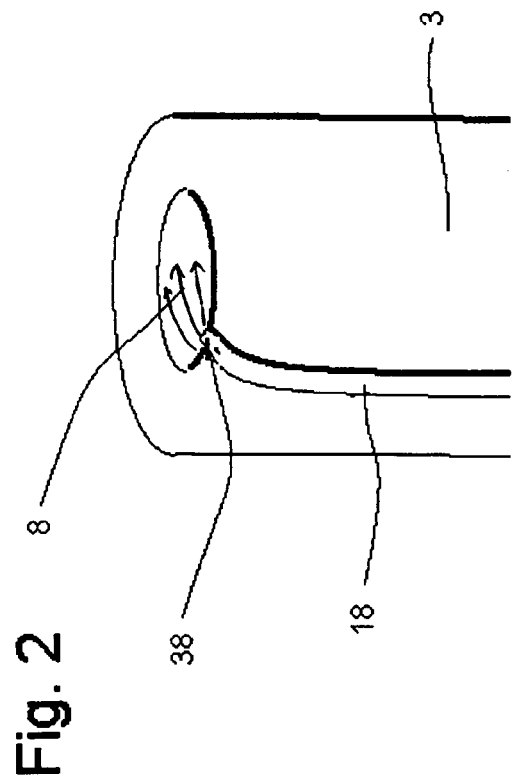

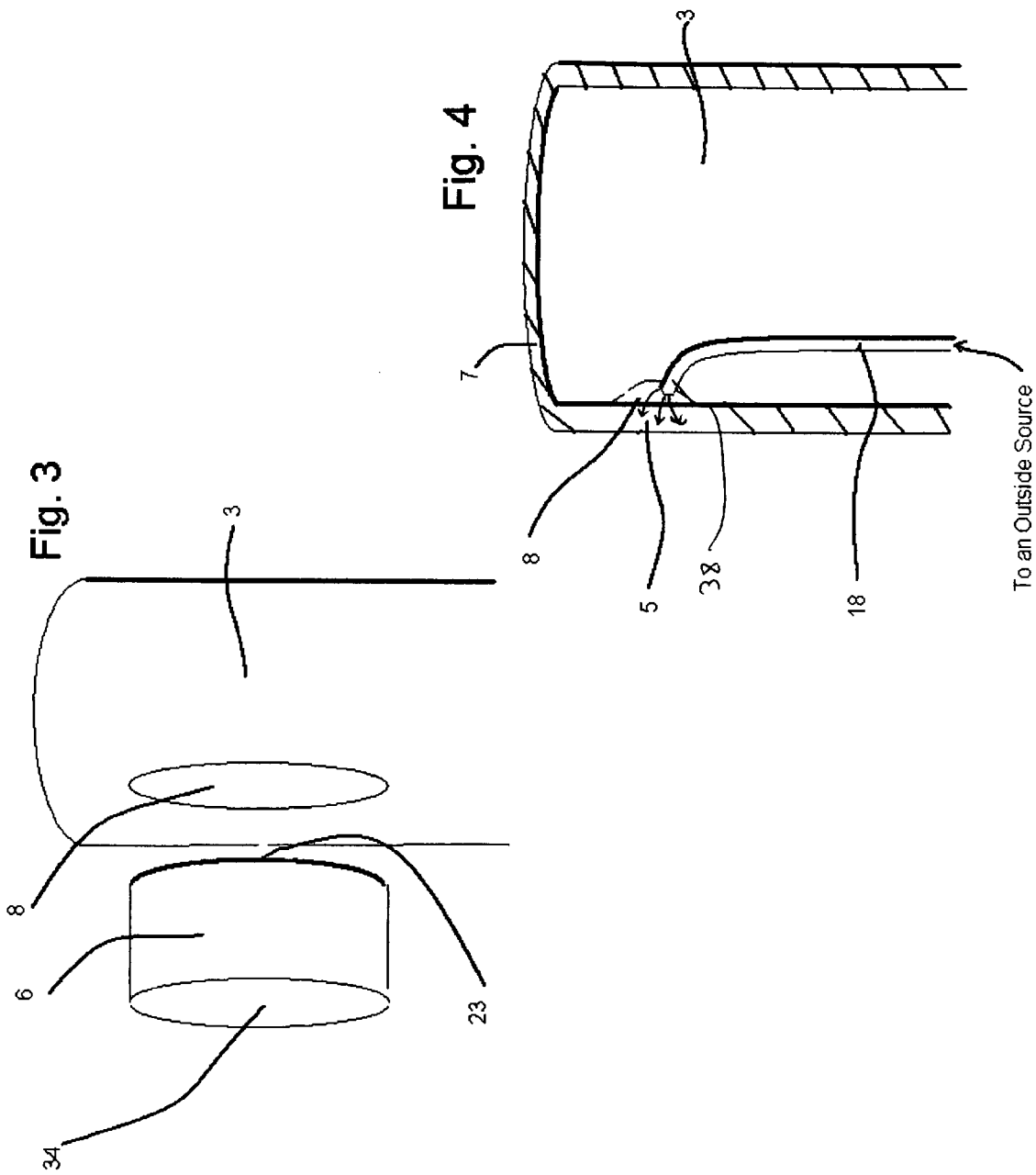

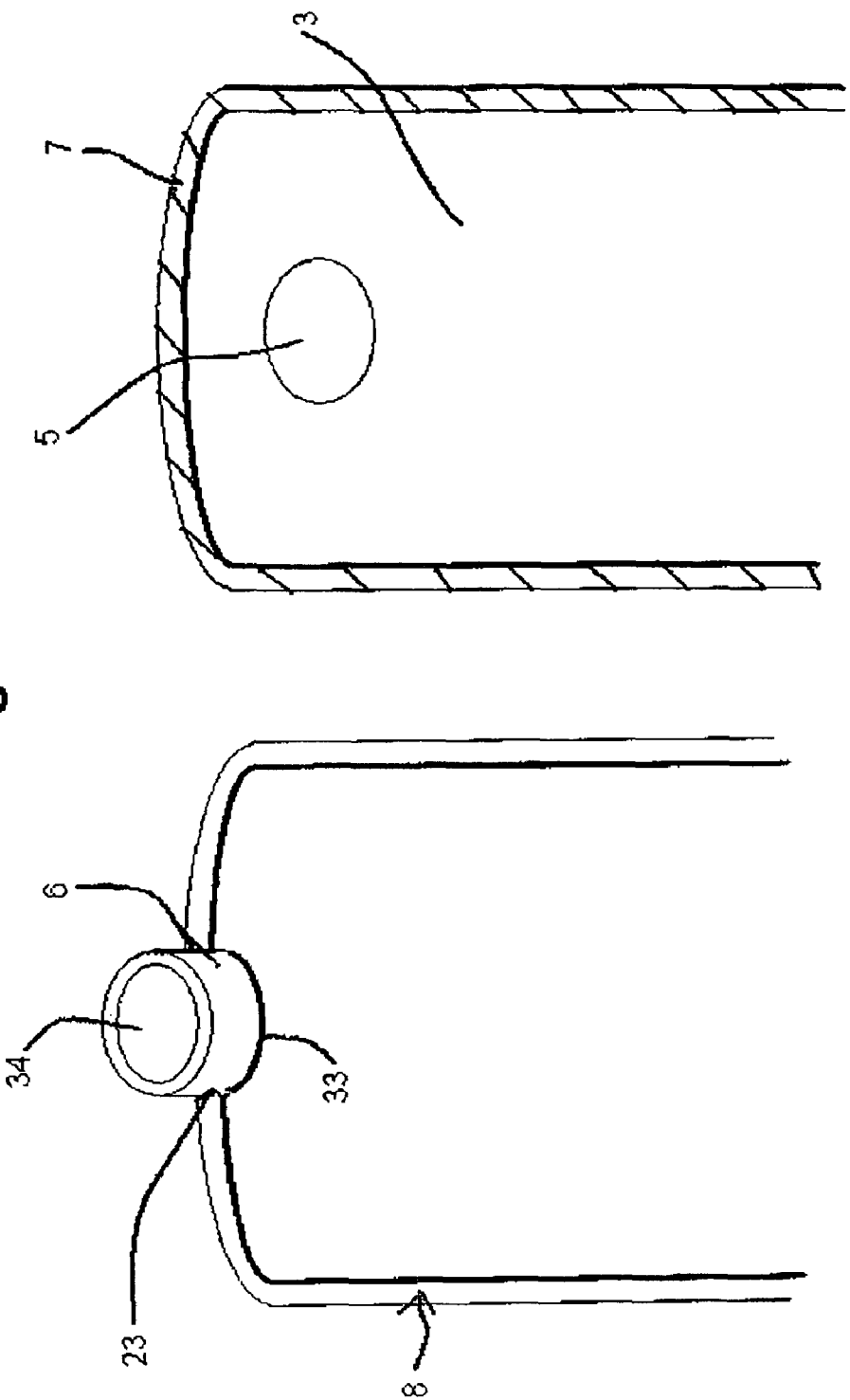

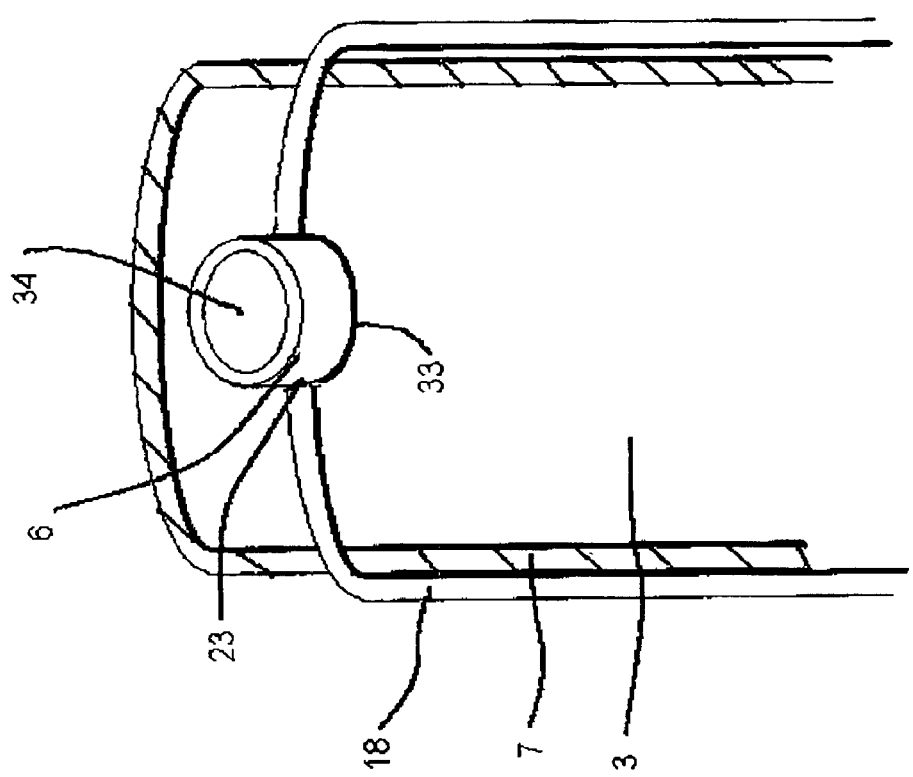

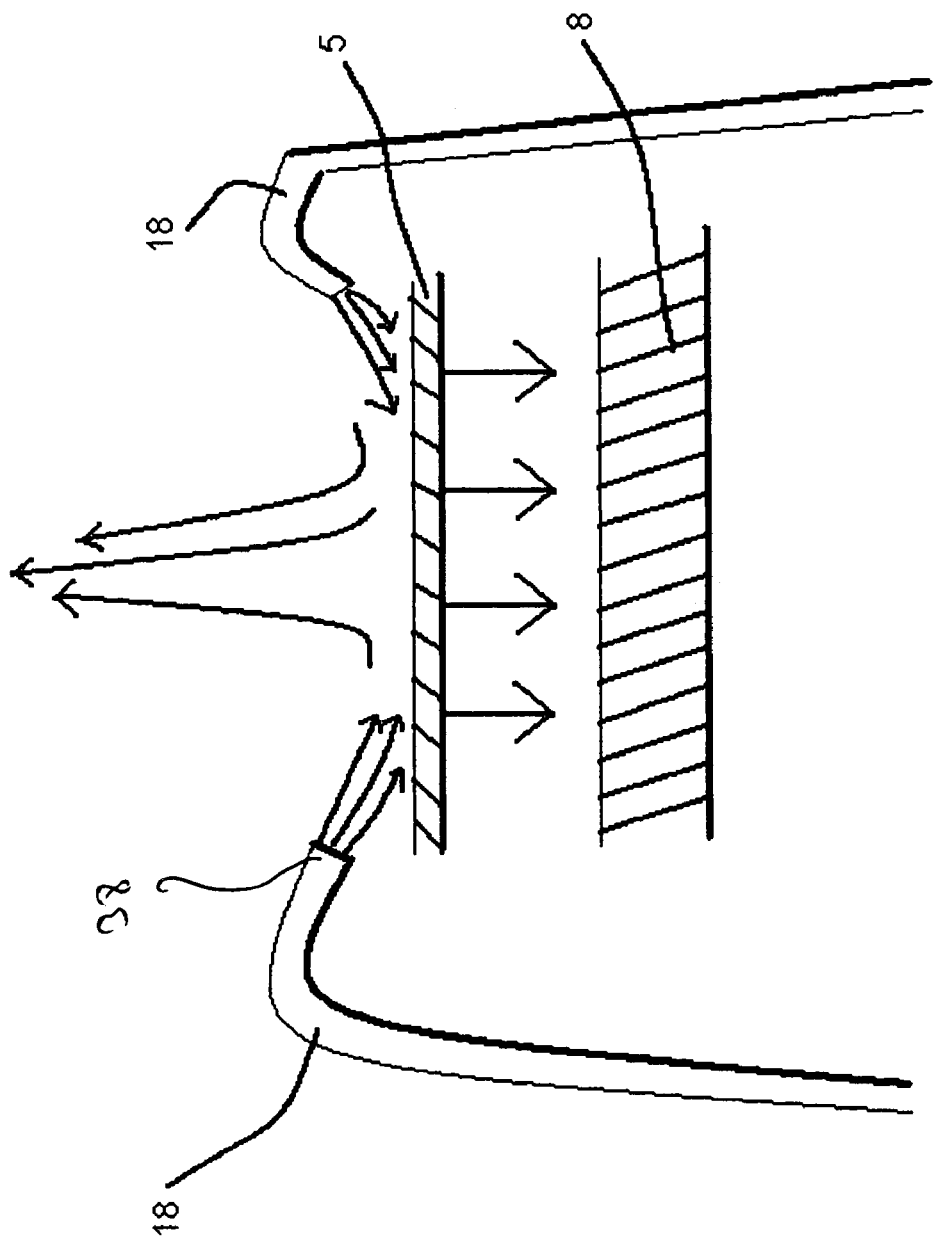

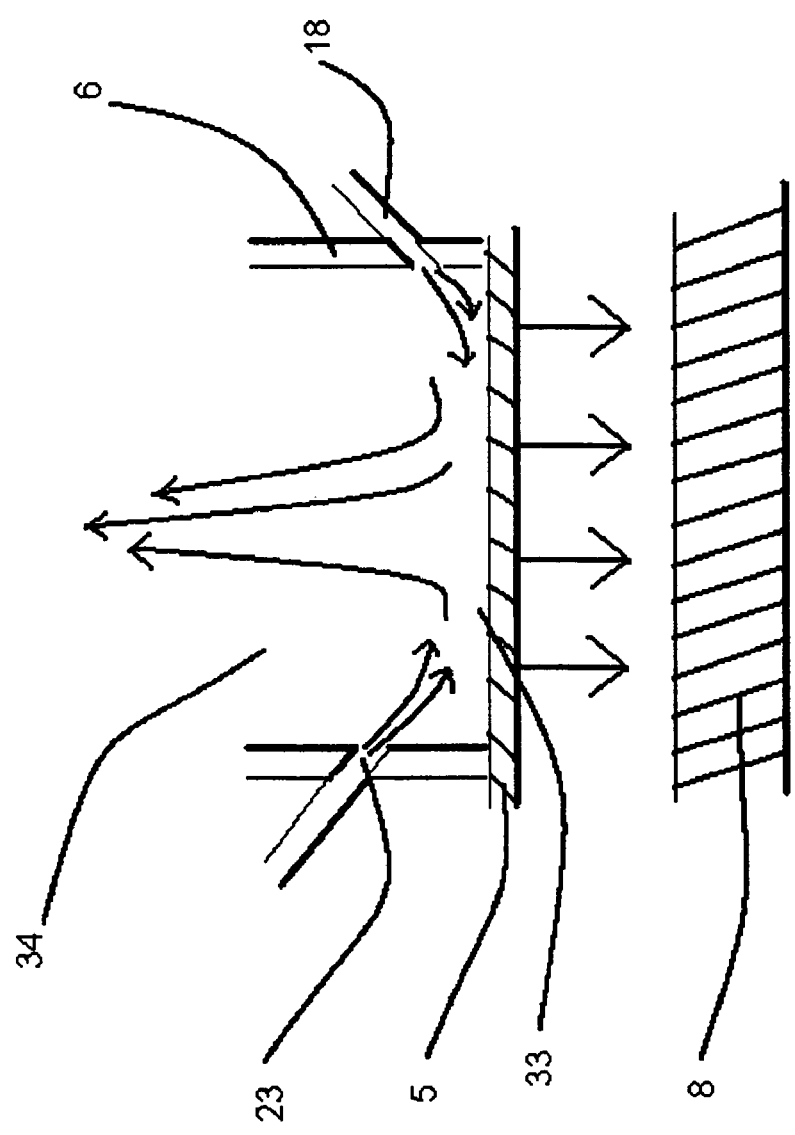

MEANS AND METHOD TO PREVENT LIQUIDS AND FLYING DEBRIS FROM BLOCKING THE VIEWING PATHWAY OF AN OPTICAL ELEMENT

CROSS REFERENCE TO RELATED APPLICATIONS

U.S. Pat. No. 5,643,175 July 1997 Adair, Edwin

U.S. Pat. No. 759,622 May 1904 Lake

U.S. Pat. No. 5,733,244 March 1998 Yasui et al

STATEMENT REGARDING FEDERALLY SPONSORED RESEARCH OR DEVELOPMENT

Not Applicable

THE NAME OF THE PARTIES TO A JOINT RESEARCH AGREEMENT

Not applicable.

INCORPORATION-BY-REFERENCE OF MATERIAL SUBMITTED ON A COMPACT DISC

Not Applicable

BACKGROUND OF THE INVENTION

The invention comprises of a means and a method to keep clean the path of vision of an optical element which may be an optical sensor or a camera, where there is flying debris or liquids that can potentially stick to the see-through cover of the optical element and clog the view of the same.

The aim of the invention is to promote better vision by the optical element by 1) avoiding bubbles between the see-through cover and the transparent surface of the optical element, and 2) blowing away any flying debris or liquids that may potentially stick to the see-through cover and compromising the visibility of the optical element. This is achieved mainly by blowing compressed gas on the see-through cover.

BRIEF SUMMARY OF THE INVENTION

The available intra-oral optical elements today are generally covered in a disposable clear plastic sheath for sanitation purposes. A problem associated with these sheaths is they lose adherence to a transparent surface of the optical element sometimes during the operation, forming a bubble between these sheaths and the transparent surface; and the image produced will become blurry. This problem is tackled with in this invention as follows. Fluid such as compressed air is blown over the see-through surface of the cover by means of a plurality of channels, pressing and helping maintain the adherence of see-through surface to transparent surface, avoiding bubbles between the see-through surface and the transparent surface, and allowing a more clear image to be viewed. This is of special importance when the cover 7 is generally elastic and flexible at least in the area of a see-through surface 5 facing a transparent surface 8.

BRIEF DESCRIPTION OF THE SEVERAL VIEWS OF THE DRAWINGS

The characteristics of the present invention will be better understood by reading the following description, given purely by way of example, and with reference to the accompanying drawings, in which:

FIG. 1 is a view of an optical element including a tube 6 positioned on the optical element 3 and attached to a channel 18 through a pore 23 located where there are flying debris 4 nearby.

FIG. 2 shows an optical element 3 including a transparent surface 8 through which it captures images and a channel 18 delivering compressed gas through a foramen 38 to the transparent surface 8 and blowing any flying debris that may otherwise stick to the transparent surface 8.

FIG. 3 shows a tube 6 with an inner opening 33 and an outer opening 34, being positioned on the transparent surface 8 of the optical camera 3.

FIG. 4 shows an optical element 3 with a transparent surface 8, being covered in a cover 7 with a see-through surface 5. The see-through surface 5 is positioned against the transparent surface 8. [FIG. 9 also shows a channel 18 delivering compressed gas to the see-through surface 5.]

FIG. 5a shows 1) a tube 6 connected through a pore 23 to a channel 18, and 2) an optical element 3 covered in cover 7.

FIG. 5b shows the tube 6 positioned on the optical element 3 so that the inner opening 33 of the tube 6 is positioned on the see-through surface 5 of the cover 7.

FIG. 6 shows two channels 18 through which compressed gas blows on the see-through surface 5 and pressing it to the transparent surface 8 and preventing any bubbles from forming.

FIG. 7 shows a tube 6 positioned on a see-through surface 5. Two channels 18 deliver compressed gas through two pores 23 to the inside of the tube 6, pressing the see-through surface 5 to the underlying transparent surface 8 and removing or avoiding any bubbles.

DETAILED DESCRIPTION OF THE INVENTION

Reference is made to Disclosure Documents #s: 592019: dated Dec. 22, 2005 and titled: Digital Imager Used in Medical/Dental Field; #592607 dated Jan. 3, 2006 and titled: Imaging Appliance Which Blows away Debris from the Field of Operation; and #595427 dated Feb. 21, 2006 and titled: Means and Method to Blow Debris Away from an Imager; filed with the U.S. Commissioner for Patents, and associated with the following specifications.

The invention comprises of a means and a method to keep clean a plurality of transparent surfaces 8, through which a plurality of images are captured by an optical element 3 which may be an optical sensor or a camera, where there is flying debris or liquids that can potentially stick to a plurality of the transparent surfaces 8 and clog the view of said optical element 3, FIG. 2. A plurality of channels 18 transfer and direct fluid such as compressed air from an outside source to blow over and keep a plurality of the transparent surfaces 8 free of debris or liquids. In a specific example of the invention, a plurality of said channels 18 direct fluid such as compressed air through a plurality of foramens 38 located at a distance close enough to—and blowing fluid such as compressed air in the direction of—a plurality of transparent surfaces 8 to effectively blow away the flying debris or liquids from the plurality of transparent surfaces 8. In another example of the invention, a plurality of channels 18 direct fluid such as compressed air through a plurality of pores 23 to a plurality of tubes 6, each tube 6 including an inner opening 33 facing a plurality of transparent surfaces 8 and an outer opening 34 through which fluid such as compressed air exits the tube 6, FIG. 1 and FIG. 3. Furthermore, a plurality of tubes 6 allow a plurality of images to pass through and reach the transparent surface 8 while the exiting fluid such as compressed air blows away any flying debris or liquids and prevents it from reaching and sticking the transparent surface 8.

Said optical element 3 can, for example, be used to monitor the hard and soft tissues, along with a variety of activities performed by an operator such as a healthcare provider, in or near the mouth.

In a specific example of the invention, said optical element 3 can be permanently or removably contained in a cover 7 which may be autoclavable and/or disposable. Said cover 7 will have adequate see-through surface 5 opposite said transparent surface 8 to allow image capture by said optical element 3, FIG. 4. A plurality of channels 18 transfer and direct fluid such as compressed air to blow over said see-through surface 5 to keep said see-through surface 5 free of debris or liquids. Said plurality of channels 18 and/or a plurality of said tubes 6 are, in one example of the invention, included as part of said cover 7 to obviate the need for handling several loose components. The operator merely places the cover 7 onto the optical element 3; the plurality of channels 8 and/or a plurality of tubes 6 are then perforce positioned accurately on the optical element 3. In a specific example of the invention, a plurality of said channels 18, running across said cover 7, are not easily bendable so as to give stiffness to and stabilize said cover 7 when placed over said optical element 3. The advantage of such a design is 1) to avoid bubbles between said transparent surface 8 and said see-through surface 5 because the cover 7 in held in position unable to move, and 2) to hold a plurality of said tubes 6 and/or said foramens 38, which are secured on said cover 7, in position with respect to the optical element 3.

In a specific example of the invention, a plurality of tubes 6, with an inner opening 33 and an outer opening 34 are positioned on said see-through surface 5 of said cover 7 with said inner opening 33 facing said see-through surface 5 which is facing said transparent surface 8, in a manner that an image can travel through said plurality of tubes 6, said see-through surface 5, said transparent surface 8, and to said optical element 3, FIG. 5a and FIG. 5b. A plurality of said channels 18, together with a plurality of said tubes 6, form an integral part which is then removably fastened over said cover 7 covering said optical element 3. This design helps stabilize said cover 7 over said optical element 3 and avoid bubbles between a plurality of transparent surfaces 8 and said see-through surface 5. This design is especially helpful to avoid bubbles between a plurality of transparent surfaces 8 and a plurality of see-through surfaces 5 if at least part of the cover 7 is flexible. A plurality of said channels 18 direct fluid such as compressed air into a plurality of said tubes 6 through a plurality of pores 23. Fluid such as compressed air which is introduced into a plurality of said tubes 6 by means of a plurality of said channels 18 exits a plurality of said tubes 6 through said outer opening 34 and prevents flying debris or liquids from entering said plurality of tubes 6, sticking to said see-through surface 5, and blocking the view of said optical element 3.

The available intra-oral optical elements today are generally covered in a disposable clear plastic sheath for sanitation purposes. A problem associated with these sheaths is they loose adherence to a transparent surface 8 sometimes during the operation, forming a bubble between these sheaths and a transparent surface 8; and the image produced will become blurry. This problem is tackled with in a specific example of the invention as follows. Fluid such as compressed air is blown over said see-through surface 5 of said cover 7 by means of a plurality of said channels 18, pressing and helping maintain the adherence of said see-through surface 5 to said transparent surface 8, avoiding bubbles between said see-through surface 5 and said transparent surface 8, and allowing a more clear image to be viewed, FIG. 6. This is of special importance when the cover 7 is generally elastic and flexible at least in the area of a see-through surface 5 facing a transparent surface 8.

In a specific example of the invention, a plurality of said tubes 6 containing at least one said pore 23 are positioned on said see-through surface 5. Fluid such as compressed air is allowed to flow into a plurality of said tubes 6 through at least one said pore 23, FIG. 7. Through said inner opening 33 of at least one said tube 6, the fluid such as compressed air will press said see-through surface 5 to said transparent surface 8 maintaining adherence between same before exiting from said outer opening 34 of said tube 6 and preventing debris or liquids to enter said tube 6 and adhere to said see-through surface 5.

In a specific example of the invention, a said cover 7 which is generally see-through and is fabricated as a fitting fits over and covers said optical element 3. A plurality of said channels 18 run along said cover 7, transferring fluid such as compressed air from an outside source to a plurality of foramens 38 that allow compressed air to exit to the outside of said channels 18. Said foramens 38 are located at a distance short enough from said see-through surface 5 facing said transparent surface 8 so that compressed air blowing from a plurality of said foramens 38 can blow over and effectively clean and blow away any debris or liquids that may otherwise stick to said see-through surface 5. In order for a plurality of said foramens 38 and for tubes 6 to accurately blow air in a desired direction, e.g. onto said see-through surface 5 or away from the see-through surface 5, they must be firmly held in position. One way to hold said foramen 38 and/or a tube 6 in position is provided by a said cover 7 that is rigid at least partially around said foramen 38 and stabilizes its position. Another example is provided by a plurality of said channels 18 that are rigid and stabilize a plurality of said foramens 38 that are located at some point on said channels 18. A third example is to fabricate at least one said channel 18 from generally flexible material. When compressed air is introduced into a said channel 18, said channel 18 expands and becomes stiff and stabilizes the position of a plurality of said foramens 38.

Also disclosed, is a method of blowing away any debris or liquids that collect around the field of vision. In a preferred example of the invention, fluid such as compressed air exiting a plurality of tubes 6 blows on the field being imaged and removes any liquids and/or debris or liquids that may have collected there. In a specific example of the invention, fluid such as compressed air also directs any such liquids and/or debris to a location where such liquids and/or debris is disposed of, for example by a saliva ejector, while an optical element 3 is imaging the field of operation. In certain surgical and/or dental procedures, blood, saliva, debris and/or liquids introduced by the operator—for example, water used in dental hand pieces and cavitron tips—collect around and obstruct the view of the field of operation. In the method disclosed in the invention, a said optical element 3 along with a plurality of said tubes 6 that blow compressed air are used to 1) prevent the view of said optical element 3 from being clogged by keeping clean the see-through surface 5 and/or the transparent surface 8, 2) blow compressed air onto the field of operation, blowing away and, for example, guiding such liquids to a location where they are disposed, for example by a suction tip positioned where said liquids are guided to; and 3) image the field of operation as disclosed above.

Even though in the examples of the invention disclosed above said optical element 3 captures the image of the objects to be viewed directly through a said transparent surface 8, it is clear to one skilled in the art that the image of the objects to be viewed—after passing through said transparent surface 8—can be reflected through a plurality of mirrors and/or a plurality of optic fibers (not shown), and directed to a plurality of sensors such as digital imaging arrays or modules which would then be located at a distance to said transparent surface 8.

Even though the examples of this invention set forth above relate mostly to the dental field, it is clear to the one skilled in the art that the invented design is also useful in many branches of medicine such as laparoscopy, hysteroscopy, and orthopedic surgery, as well as many industrial applications where the need to stop and clean said transparent surface 8 from debris or liquids is obviated. One skilled in the art will appreciate that the present invention can be practiced by other, than the described embodiments, which are presented here for purposes of illustration and not of limitation, and the present invention is limited only by the claims that follow.

What I claim is:

1. An optical element including a plurality of transparent surfaces which are used to capture a plurality of images, said optical element being covered in a cover including at least one see-through surface generally positioned opposite at least one of said plurality of transparent surfaces, said cover further including a plurality of channels that direct compressed gas from an outside source to a point near said at least one see-through surface, wherein at least part of said at least one see-through surface or an area adjacent to it is flexible so that when the compressed gas blows over it, said at least one see-through surface is pressed against the respective opposite general area of said at least one of said plurality of transparent surfaces, enhancing adherence and avoiding bubbles between at least part of said at least one see-through surface and the respective opposite general area of said at least one of said plurality of transparent surfaces for better imaging quality by said optical element.

2. The optical element according to claim 1 in which the plurality of channels lead the compressed gas to at least one tube with an inner opening and an outer opening, said at least one tube being positioned on said cover so that said inner opening of said at least one tube is located on and faces said at least one see-through surface.

3. The optical element according to claim 1 in which said cover is disposable.

4. An optical element including a plurality of transparent surfaces which are used to capture a plurality of images, said optical element being covered in an autoclavable cover including at least one see-through surface generally positioned opposite at least one of said plurality of transparent surfaces, said cover further including a plurality of channels that direct compressed gas from an outside source to a point near said at least one see-through surface, wherein at least part of said at least one see-through surface or an area adjacent to it is flexible so that when the compressed gas blows over it, said at least one see-through surface is pressed against the respective opposite general area of said at least one of said plurality of transparent surfaces, enhancing adherence and avoiding bubbles between at least part of said at least one see-through surface and the respective opposite general area of said at least one of said plurality of transparent surfaces for better imaging quality by said optical element.

5. The optical element according to claim 4 in which the plurality of channels lead the compressed gas to at least one tube with an inner opening and an outer opening, said at least one tube being positioned on said cover so that said inner opening of said at least one tube is located on and faces said at least one see-through surface.

6. An optical element including a plurality of transparent surfaces which are used to capture a plurality of images, said optical element being covered in a disposable cover including at least one see-through surface generally positioned opposite at least one of said plurality of transparent surfaces, said optical element further including a plurality of channels directing compressed gas from an outside source to a point near said at least one see-through surface, wherein at least a part of said at least one see-through surface or an area adjacent to it is flexible so that when the compressed gas blows over it, said at least one see-through surface is pressed against the respective opposite general area of said at least one of said plurality of transparent surfaces, enhancing adherence and avoiding bubbles between at least part of said at least one see-through surface and the respective opposite general area of said at least one of said plurality of transparent surfaces for better imaging quality by said optical element.

7. The optical element according to claim 6 in which the plurality of channels lead the compressed gas to at least one tube with an inner opening and an outer opening, said at least one tube being positioned on said cover so that said inner opening of said at least one tube is located on and faces said at least one see-through surface.

8. An optical element including a plurality of transparent surfaces which are used to capture a plurality of images, said optical element being covered in an autoclavable cover including at least one see-through surface generally positioned opposite at least one of said plurality of transparent surfaces, said optical element further including a plurality of channels directing compressed gas from an outside source to a point near said at least one see-through surface wherein at least a part of said at least one see-through surface or an area adjacent to it is flexible so that when the compressed gas blows over it, said at least one see-through surface is pressed against the respective opposite general area of said at least one of said plurality of transparent surfaces, enhancing adherence and avoiding bubbles between at least part of said at least one see-through surface and the respective opposite general area of said at least one of said plurality of transparent surfaces for better imaging quality by said optical element.

9. The optical element according to claim 8 in which the plurality of channels lead the compressed gas to at least one tube with an inner opening and an outer opening, said at least one tube being positioned on said cover so that said inner opening of said at least one tube is located on and faces said at least one see-through surface.

10. An optical element including a plurality of transparent surfaces which are used to capture a plurality of images, said optical element being covered in a cover including at least one see-through surface generally positioned opposite at least one of said plurality of transparent surfaces, said optical element further including a plurality of channels directing compressed gas from an outside source to a point near said at least one see-through surface, wherein at least a part of said at least one see-through surface or an area adjacent to it is flexible so that when the compressed gas blows over it, said at least one see-through surface is pressed against the respective opposite general area of said at least one of said plurality of transparent surfaces, enhancing adherence and avoiding bubbles between at least art of said at least one see-through surface and the respective opposite general area of said at least one of said plurality of transparent surfaces for better imaging quality by said optical element.

11. The optical element according to claim 10 in which the plurality of channels lead the compressed gas to at least one tube with an inner opening and an outer opening, said at least one tube being positioned on said cover so that said inner opening of said at least one tube is located on and faces said at least one see-through surface.

* * * * *